United States Patent [19]
Takeuchi et al.

[11] Patent Number: 4,924,869
[45] Date of Patent: May 15, 1990

[54] ULTRASONIC DIAGNOSTIC SYSTEM

[75] Inventors: Yasuhito Takeuchi; Takao Higashiizumi; Motoyoshi Ando; Yoshiro Tamezumi, all of Tokyo, Japan

[73] Assignee: Yokogawa Medical Systems, Limited, Tokyo, Japan

[21] Appl. No.: 254,500
[22] PCT Filed: Feb. 27, 1987
[86] PCT No.: PCT/JP87/00130
§ 371 Date: Aug. 23, 1988
§ 102(e) Date: Aug. 23, 1988
[87] PCT Pub. No.: WO87/05199
PCT Pub. Date: Sep. 11, 1987

[30] Foreign Application Priority Data
Feb. 28, 1986 [JP] Japan .................. 61-43515

[51] Int. Cl.$^5$ ................................. A61B 8/00
[52] U.S. Cl. ............... 128/660.05; 128/662.01; 73/861.25
[58] Field of Search ........ 128/661.01, 660.05, 128/662.01, 662.08–662.10; 73/861.25

[56] References Cited
U.S. PATENT DOCUMENTS

| | | | |
|---|---|---|---|
| 4,062,237 | 12/1977 | Fox | 128/662.01 X |
| 4,563,899 | 1/1986 | Nakamura | 128/662.01 X |
| 4,598,589 | 7/1986 | Riley et al. | 128/661.01 X |
| 4,622,978 | 11/1986 | Matsuo et al. | 128/662.01 X |
| 4,664,122 | 5/1987 | Yano | 128/661.01 |
| 4,817,617 | 4/1989 | Takeuchi et al. | 128/661.01 X |

Primary Examiner—Francis Jaworski
Attorney, Agent, or Firm—Moonray Kojima

[57] ABSTRACT

To apply our new invention in the most preferred application mode, we used an ultrasonic diagnostic system that can instantaneously switch over to the CW Doppler method or B-mode imaging method when both methods are combined using a commonly applicable array probe. The ultrasonic diagnostic system based on this new invention is configured with the following features:

Dividing multiple vibrating elements of a commonly applicable array probe (3) into two groups, (3T) and (3R), and connecting the first vibrating element group (3T) to the first transmitting driver (2T) to which low voltage is supplied by the power supply (4), and connecting the second vibrating element group (3R) to the second transmitting driver (2R) to which high voltage is supplied by the power supply (4). For applying the CW Doppler method:

Driving the first vibrating element group by the first transmitting driver with a low-voltage continuous wave to transmit a continuous ultrasonic wave and receive an echo signal with the second vibrating element group; For applying the B-mode imaging method:

Driving the second vibrating element group by the second transmitting driver using a high-voltage pulse wave to transmit an ultrasonic pulse wave and receive an echo signal with the second vibrating element group.

2 Claims, 1 Drawing Sheet

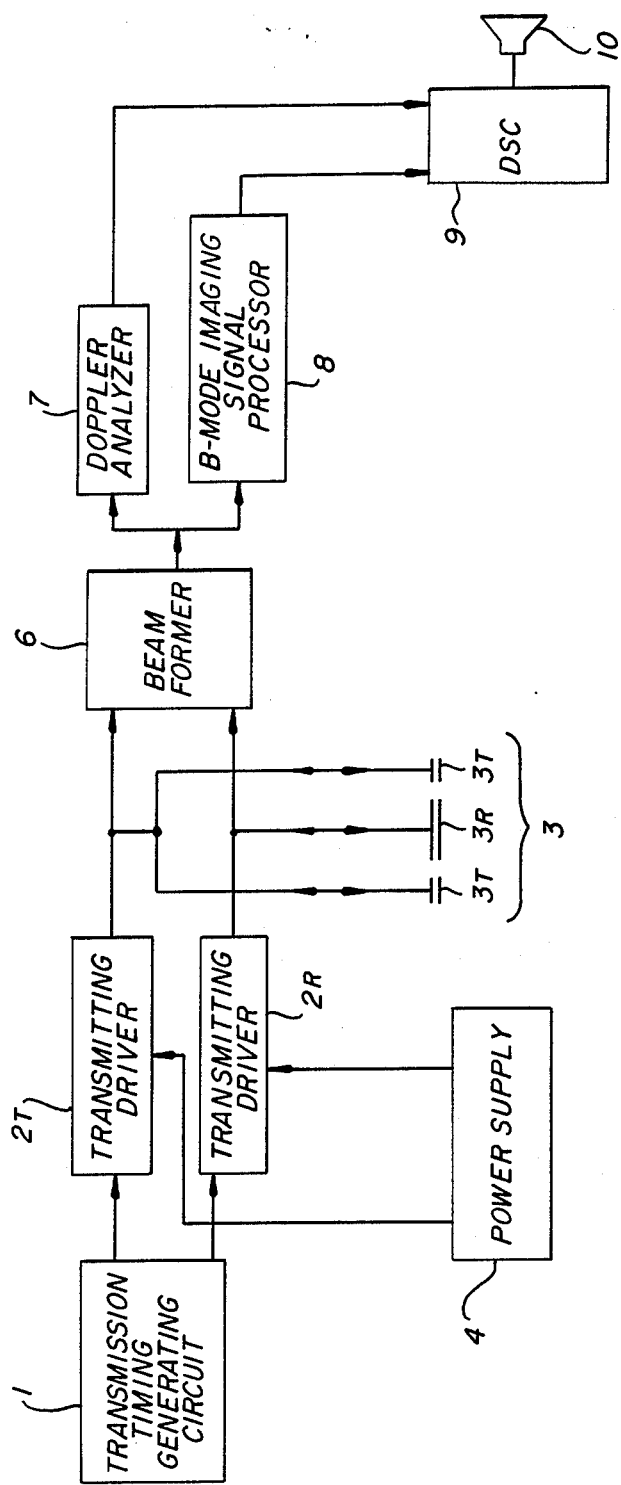

even the #

ULTRASONIC DIAGNOSTIC SYSTEM

TECHNICAL FIELD

This new invention is basically an ultrasonic diagnostic system operated with an array probe commonly used for both the CW Doppler and B-mode imaging methods.

BACKGROUND ART

Using the CW Doppler method in an ultrasonic diagnostic system internally exposes a subject to a continuous ultrasonic wave, and determines the speed of an object in motion, such as the blood flow, by using the Doppler effect of ultrasonic echo signals. The B-mode imaging method applies ultrasonic pulses to a subject and displays a tomographic image of the subject according to the intensity of a ultrasonic echo. The B-mode imaging method is often applied together with the CW Doppler method for convenience because B-mode imaging provides an operator with tomographic images of the subject. The CW Doppler and B-mode imaging methods are conventionally applied using separate probes. It would be much more convenient if a probe, such as the array probe used for B-mode imaging, could be commonly applied to both methods. However, such application poses the following problems.

The B-mode imaging method uses a transmission waveform having a narrow pulse width to improve resolution. Note not decreased transmission power means decreased echo reception power, which adversely affects the signal-to-noise ratio and picture quality. To cope with this, the transmission pulse amplitude must be increased to increase the transmission power. To increase the transmission pulse amplitude, the output voltage of the transmitting driver must be raised (to 80 V or higher, for example). Conversely, the CW Doppler method utilizes a continuous wave for signal transmission. Therefore, the output voltage for the transmitting driver must also be lowered (to several volts, for example) for two reasons: a safe limits for living bodies, and operating power limits for the probe.

When applying the CW Doppler and B-mode imaging methods together using a commonly applicable array probe, tomographic images of the subject are required for observation while measuring the blood flow by using the CW Doppler method. Temporarily switching to the B-mode imaging method and returning to the CW Doppler method immediately thereafter to resume blood flow measurement is also required. To enable this, the output voltage of the transmitting driver must be instantaneously switched to high voltage, low voltage, and back to the high voltage. For the configuration needed to enable such changeover, a transmitting driver to which high voltage is supplied must be considered, and by controlling the output amplitude of its final stage amplifier to output low and high voltages. In this case, if small amplitude output must be provided in the CW mode from a high-voltage power supply, a problem is posed by the excessively high temperatures generated in the final stage amplifier. Consequently, to solve this problem, switching the supply voltage must be considered so that the supply voltage to the transmitting driver is lowered in correspondence to low-voltage output or is raised for high-voltage output. However, this switching method requires the charging and discharging of bypass capacitors positioned in the circuits, which make instantaneous switching difficult. It takes at least tens to several hundreds of miliseconds for effective switching. This means that such a transitional pause must be placed before and after B-mode imaging, making it difficult to apply the B-mode imaging method without practically interrupting the application of the CW Doppler method.

DISCLOSURE OF THE INVENTION

The object of this new invention is to provide a ultrasonic diagnostic system that can instantaneously switch over to the CW Doppler method B-mode imaging method when the CW Doppler method and B-mode imaging method are used together with a commonly applicable array probe. To apply our new invention in the preferred application mode, we used an ultrasonic diagnostic system having the following features:

Dividing multiple vibrating elements of a commonly applicable array probe (3) into groups (3T) and (3R), and connecting the first vibrating element group (3T) to the first transmitting driver (2T) to which low voltage is supplied by the power supply (4), and connecting the second vibrating element group (3R) to the second transmitting driver (2R) to which high voltage is supplied by the power supply (4). For applying the CW Doppler method:

Driving the first vibrating element group by the first transmitting driver with a continuous wave using low voltage to transmit a continuous ultrasonic wave and receive an echo signal with the second vibrating element group. For applying the B-mode imaging method:

Driving the second vibrating element group by the second transmitting driver with a pulse wave using high voltage to transmit an ultrasonic pulse wave and receive an echo signal with the second vibrating element group.

BRIEF DESCRIPTION OF THE DRAWING

The drawing shows a block diagram of the preferred application mode of an ultrasonic diagnostic system based on this new invention.

DESCRIPTION OF PREFERRED EMBODIMENTS

The application of this new invention will be described in detail by referring to the attached drawing. The drawing shows a block diagram of the preferred application mode of an ultrasonic diagnostic system based on this new invention. In said diagram, number 1 indicates a transmission timing generating circuit that determines the timing for an ultrasonic wave transmission, and which issues respective trigger signals to first transmitting driver 2T and second transmitting driver 2R. According to the trigger signals, transmitting drivers 2T and 2R issue a drive signal for ultrasonic wave transmission to array probe 3, which consists of multiple vibrating elements. Said vibrating elements of array probe 3 are divided into two groups (3T and 3R). The drive signal from first transmitting driver 2T is sent to first element group 3T, and the drive signal from second transmitting driver 2R is sent to second element group 3R. Although the diagram shows the individual element groups in a simplified way i.e. as boxes, it is to be understood that, each group consists of a plurality of elements. Drive signals sent to these element groups by transmitting drivers 2T and 2R are phase-controlled with individual vibrating elements by transmission timing generating circuit 1 in response to the transmission direction of the ultrasonic beam. Number 4 indicates the power supply for transmitting drivers 2T and 2R that supplies low voltage to 2T and a high voltage to 2R.

Said low voltage refers to the approximate value of several volts suitable for the CW Doppler method, and said high voltage refers to the approximate value of 80 V or higher suitable for the B-mode imaging method. These supply voltages represent the peak values of transmitting drivers 2T and 2R. First transmitting driver 2T outputs a drive signal for a continuous wave according to the CW Doppler method or a drive signal for a pulse wave according to the B-mode imaging method. Second transmitting driver 2R only operates during the B-mode imaging method and issues a drive signal for a pulse wave to second element group 3R.

Number 6 indicates a beam former, which receives a signal from array probe 3 to form beams. For the CW Doppler method, beam former 6 inputs signals after beam forming to Doppler analyzer 7. For the B-mode imaging method, beam former 6 input these signals to B-mode imaging signal processor 8. Output signals from Doppler analyzer 7 and B-mode imaging signal processor 8 are respectively written as spectral and tomographic image data to a digital scan converter (or simply DSC) 9. The data written to DSC 9 is displayed as images on CRT display unit 10. The above-described ultrasonic diagnostic system performs the CW Doppler method and B-mode imaging method as follows. First, when measuring the blood flow according to the CW Doppler method, first transmitting driver 2T causes the CW ultrasonic wave to be generated by applying a low-voltage drive signal of a continuous wave to first element group 3T of probe 3 according to the timing signal generated by the transmission timing generating circuit 1. The echo signal corresponding to said CW ultrasonic wave is received by second element group 3R, which is then inputted to Doppler analyzer 7 after being formed through beam former 6. The results of analysis by Doppler analyzer 7 are written to DSC 9 as spectral images. The spectral images written to DSC 9 are then read out as required for display on display unit 10.

If tomographic images of a subject are desired while interrupting the measurement of the blood flow using the CW Doppler method by the B-mode imaging method, a switching operation is executed by an unillustrated sequence control. Transmission timing generating circuit 1, outputs a trigger signal for controlling B-mode imaging to transmitting drivers 2T and 2R when it receives the switching signal. Accordingly, transmitting drivers 2T and 2R respectively output a low-voltage pulse and high-voltage pulse to first element group 3T and second element group 3R as respective drive signals. Both element groups respectively generate an ultrasonic pulse according to these drive signals. The reflected waves to these ultrasonic pulses are received by both element groups 3T and 3R, and such received signals are subjected to beam-forming through beam former 6, processing by B-mode imaging signal processor 8, and writing to DSC 9. Such ultrasonic pulse transmission and echo reception are done while scanning the desired section of the subject with an ultrasonic beam. The image data for one screen is written to DSC 9. Furthermore, ultrasonic pulse transmission and reception for B-mode imaging are done by the second vibrating element group alone, or ultrasonic pulse transmission is done by the second vibrating element group and echo reception may done by both element groups. When receiving the image data for one screen, the system is switched to the CW Doppler mode by sequence control. As previously described, when a continuous wave is transmitted by the CW Doppler method, only transmitting driver 2T(which is supplied with low voltage) is driven, while second transmitting driver 2R(which receives high supply voltage) is driven to transmit a pulse wave by using the B-mode imaging method. Therefore, the appropriate transmitting power is obtained for either method, and because no supply voltage switching is required for changeover, instantaneous shifting between the CW Doppler method and the B-mode imaging method and vice versa is made possible.

We have described the best application mode for this new invention. This invention may be applied with ease in other specifc forms by knowledgeable persons in applicable technical fields without departing from the spirit or essential characteristics of the following claims.

We claim:

1. An ultrasonic diagnostic system comprising
an array of ultrasonic vibrating elements comprising a first group of elements and a second group of elements;
first drive means for supplying low voltage continuous wave drive signals to said first group of elements for effecting a CW Doppler mode of imaging;
second drive means for supplying high voltage pulse wave drive signals to said second group of elements for effecting a B-mode of imaging;
first signal processing means for processing signals according to echo signals received by said second group of elements while effecting said CW Doppler mode of imaging;
second signal processing means for processing signals according to echo signals received by at least said second group of elements while effecting said B-mode of imaging; and
timing means for selectively causing said first drive means to supply said low voltage continuous wave drive signals to effect said CW Doppler mode of imaging, and for selectively causing said second drive means to supply said high voltage pulse wave drive signals to effect said B-mode of imaging, so that in said CW Doppler mode the first signal processing means obtains signals from said second group of elements and ion said B-mode the second processing means obtains signals from both said first and second group of elements.

2. The system of claim 1, wherein said timing means comprises means for causing said first drive means to supply low voltage continuous wave drive signals to said first group of elements during said B-mode of imaging while concurrently interrupting said CW Doppler mode of imaging.

* * * * *